United States Patent
Watanabe et al.

(10) Patent No.: US 8,784,381 B2
(45) Date of Patent: Jul. 22, 2014

(54) DRUG INJECTION DEVICE WITH ACCELERATION SENSOR FOR DETECTING ABNORMAL OPERATION

(75) Inventors: Atsushi Watanabe, Ehime (JP); Seiji Kikuchi, Ehime (JP); Tsuguhiro Kondo, Ehime (JP)

(73) Assignee: Panasonic Healthcare Co., Ltd., Ehime (JP)

( * ) Notice: Subject to any disclaimer, the term of this patent is extended or adjusted under 35 U.S.C. 154(b) by 62 days.

(21) Appl. No.: 13/148,364

(22) PCT Filed: Mar. 1, 2010

(86) PCT No.: PCT/JP2010/001380
§ 371 (c)(1),
(2), (4) Date: Aug. 8, 2011

(87) PCT Pub. No.: WO2010/100883
PCT Pub. Date: Sep. 10, 2010

(65) Prior Publication Data
US 2011/0306927 A1 Dec. 15, 2011

(30) Foreign Application Priority Data
Mar. 4, 2009 (JP) .................................. 2009-050052

(51) Int. Cl.
*A61M 37/00* (2006.01)
*A61M 5/32* (2006.01)
(52) U.S. Cl.
USPC .......................................... 604/154; 604/197
(58) Field of Classification Search
USPC .......... 604/110, 111, 131–157, 196–198, 223
See application file for complete search history.

(56) References Cited

U.S. PATENT DOCUMENTS

| | | | |
|---|---|---|---|
| 5,989,221 A | 11/1999 | Hjertman | |
| 2001/0053888 A1* | 12/2001 | Athanasiou et al. | 604/154 |
| 2003/0105430 A1* | 6/2003 | Lavi et al. | 604/136 |
| 2004/0049156 A1 | 3/2004 | Langley et al. | |

FOREIGN PATENT DOCUMENTS

| | | |
|---|---|---|
| JP | 11-513586 | 11/1999 |
| JP | 2004-516102 | 6/2004 |

OTHER PUBLICATIONS

Meike, Roger. "Location, Location, Location (Accelerometer)." Nov. 10, 2008. Retrieved on Nov. 28, 2012. https://blogs.oracle.com/roger/entry/location_location_location_accelerometer.*
International Search Report issued May 25, 2010 in International (PCT) Application No. PCT/JP2010/001380.

* cited by examiner

*Primary Examiner* — Nathan R Price
(74) *Attorney, Agent, or Firm* — Wenderoth, Lind & Ponack, L.L.P.

(57) ABSTRACT

A drug injection device includes a main body case having an injection needle let-in/let-out opening, a drug syringe mounting component that is provided inside the main body case and in which a drug syringe is mounted, a piston that is movable with respect to the drug syringe mounting component, a drive mechanism that drives the piston, a controller that is electrically connected to the drive mechanism, and an acceleration sensor that is electrically connected to the controller. This drug injection device allows the injection of a drug to be carried out safely and properly.

10 Claims, 8 Drawing Sheets

DRUG INJECTION DEVICE WITH ACCELERATION SENSOR FOR DETECTING ABNORMAL OPERATION

BACKGROUND OF THE INVENTION

I. Technical Field

The present invention relates to a drug injection device.

II. Description of the Related Art

A conventional drug injection device has a main body case, an injection needle let-in/let-out opening that is an opening for letting an injection needle in and out of the main body case, a drug syringe mounting component that is provided inside the main body case and in which a drug syringe is mounted, a piston that is able to move with respect to this drug syringe mounting component, a drive mechanism that drives the piston, and a control circuit that is electrically connected to this drive mechanism. With this drug injection device, when the piston is moved so that sealing rubber within the drug syringe mounting component is pushed, the drug is automatically injected into the patient's body through an injection needle mounted at the distal end side of the drug syringe (see, for example, Kohyo (Japanese Unexamined Patent Publication) No. H11-513586).

However, the injection of the drug is sometimes not carried out properly with a conventional drug injection device. For example, if the user's hand should shake for some reason during drug injection, then the drug cannot be properly injected at the targeted site on the body.

In view of this, it is an object of the present invention to provide a drug injection device with which the injection of a drug can be carried out properly.

SUMMARY OF THE INVENTION

The drug injection device pertaining to the present invention comprises a main body case, a drug syringe mounting component, a piston, a drive mechanism, a controller, and an acceleration sensor. The main body case has an injection needle let-in/let-out opening. The drug syringe mounting component is provided inside the main body case, and allows a drug syringe to be mounted therein. The piston is movable with respect to the drug syringe mounting component. The drive mechanism drives the piston. The controller is electrically connected to the drive mechanism. The acceleration sensor is electrically connected to the controller.

As mentioned above, with the drug injection device of the present invention, abnormal operation of the main body case due to, for example, hand shake, can be detected by the acceleration sensor, so the injection of a drug can be carried out properly.

DETAILED DESCRIPTION OF THE INVENTION

1. Embodiment 1.1 Overall Configuration of Drug Injection Device 100

The drug injection device 100 pertaining to an embodiment of the present invention will now be described through reference to the appended drawings.

Figure 1:
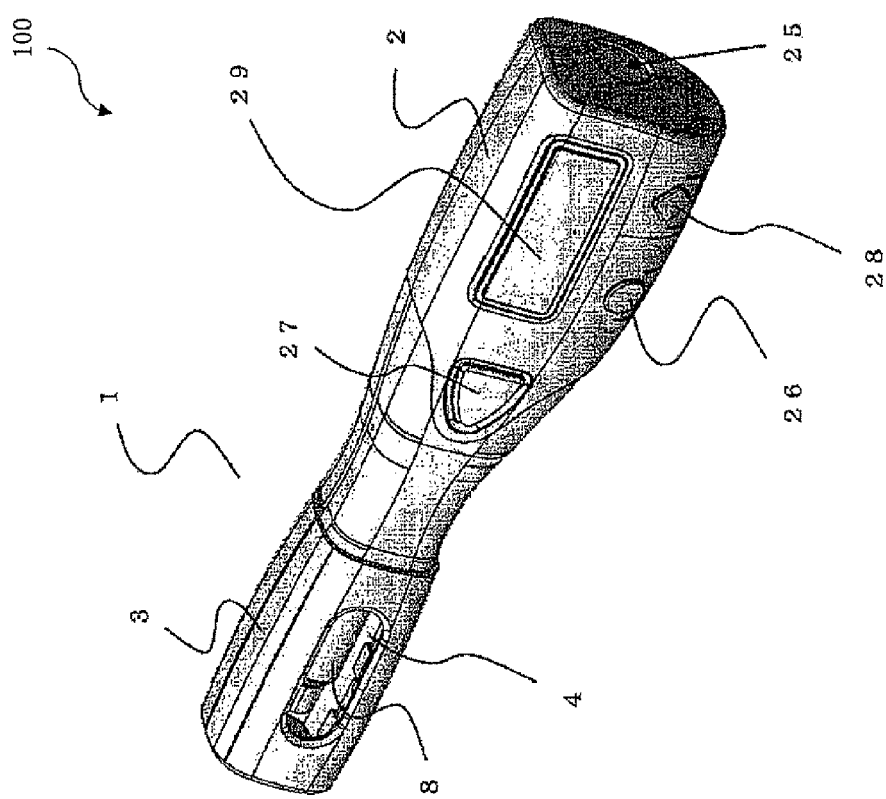
FIG. 1 is an oblique view of the drug injection device pertaining to an embodiment of the present invention.

The drug injection device 100 shown in FIG. 1 comprises a main body case 1. The main body case 1 is made up of a holder 2 and a distal end cap 3 attached on the distal end side, which is a drug injection side of the holder 2.

The distal end cap 3 is configured such that it can be attached to and removed from the holder 2. Also, the distal end cap 3 is provided with a check window 4 on its outer peripheral part. The distal end cap 3 is further provided on its distal end side with an injection needle let-in/let-out opening 5 for letting an injection needle in and out of the distal end cap 3, as shown in FIG. 2.

The holder 2 is provided with various operating buttons on its outer peripheral part. More specifically, a power button 25 is provided at the rear end of the holder 2, and an air bleed button 26, a drug injection button 27, and a stop button 28 are provided on the outer periphery of the holder 2. These operating buttons are connected to a controller 23 as discussed below. The user presses these buttons to execute various operations of the drug injection device 100 (discussed below). The holder 2 also has a display component 29 on its outer peripheral part, and the operating state of the drug injection device 100, notifications to the user, and so forth are displayed as discussed below.

Figure 2:
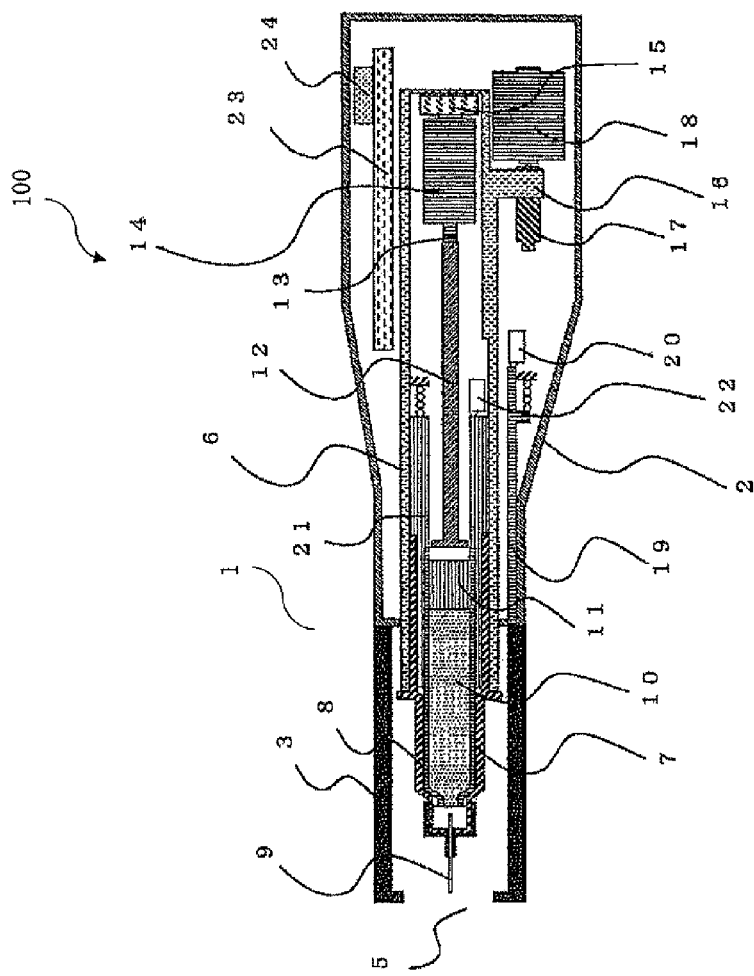
FIG. 2 is a cross section of this drug injection device.

As shown in FIG. 2, the drug injection device 100 comprises inside the holder 2 a drug syringe mounting component 6 (on the distal end cap 3 side), a piston 12, a piston drive motor 14 (drive mechanism), the controller 23, and an acceleration sensor 24 (such as a three-dimensional acceleration sensor).

A drug syringe 7 is housed in the drug syringe mounting component 6. After the drug syringe 7 has been put in place, the outer periphery of the drug syringe 7 is covered with a syringe cover 8.

As shown in FIG. 2, the drug syringe 7 mounted in the drug syringe mounting component 6 has an injection needle 9 mounted on its distal end side. The interior of the drug syringe 7 is filled with a drug 10 at a pharmaceutical manufacturer or the like. A rubber seal 11 is mounted at the rear end opening of the drug syringe 7.

The piston 12 is disposed so that it can move back and forth inside the drug syringe mounting component 6 facing the rubber seal 11. A bolt 13 is inserted from the rear end side of the piston 12 (the opposite side from the drug injection side) all the way into the piston 12.

The piston drive motor 14 is attached on the rear end side of the bolt 13, and rotationally drives the bolt 13. Rotation of the bolt 13 causes the male threads around the outer periphery of the bolt 13 to spirally mesh with female threads provided inside the piston 12, and the piston 12 pushes the rubber seal 11 forward, that is, to the drug injection side. As a result of this operation, the drug 10 flows out of the injection needle 9. Also, an encoder 15 is connected to the piston drive motor 14.

Rotation of the piston drive motor 14 is detected by the encoder 15, and this allows the amount of movement of the piston 12 to be detected.

Figure 3:
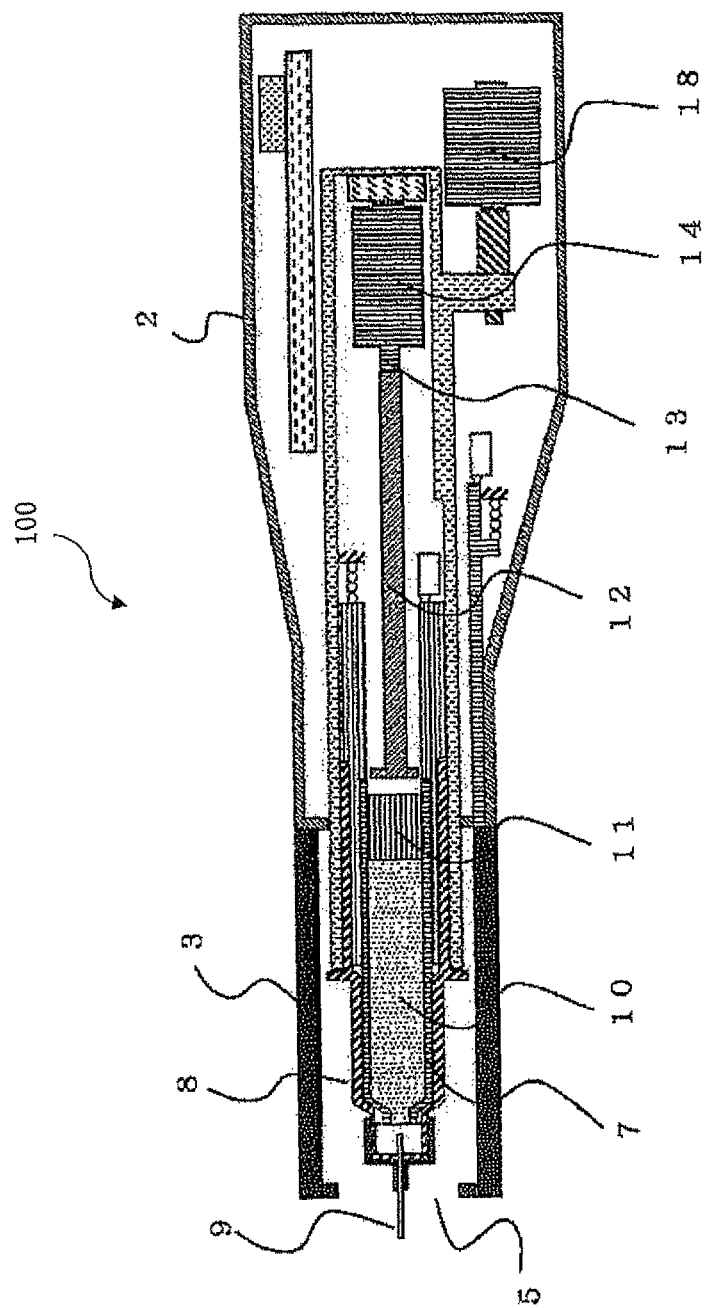
FIG. 3 is a cross section of this drug injection device.

The drug syringe mounting component 6 itself is configured so as to be able to move back and forth with respect to the injection needle let-in/let-out opening 5. More specifically, a bolt 17 is inserted into a female thread 16 provided to the rear of the drug syringe mounting component 6, and a needle deployment/retraction drive motor 18 is attached to this bolt 17. The drive provided by the needle deployment/retraction drive motor 18 causes the drug syringe mounting component 6 itself to move to the injection needle let-in/let-out opening 5 side as shown in FIG. 3. As a result, the injection needle 9 sticks out from the injection needle let-in/let-out opening 5. As will be discussed below, the air bleed operation and the injection of the drug 10 are carried out in a state in which the injection needle 9 protrudes from the injection needle let-in/let-out opening 5.

A number of switches are further housed in the holder 2 of the main body case 1.

More specifically, a distal end cap detection switch 20 is disposed toward the distal end of the holder 2. The distal end cap detection switch 20 is attached to the rear end of an operating rod 19 provided to the outer periphery of the drug syringe mounting component 6. When the distal end cap 3 is mounted to the distal end of the holder 2, the operating rod 19 is pushed to the rear end side, and the distal end cap detection switch 20 is actuated, which causes the controller 23 (discussed below) to detect the mounting of the distal end cap 3.

Also, a syringe cover detection switch 22 is disposed in the drug syringe mounting component 6. The syringe cover detection switch 22 is attached to the rear end of an operating rod 21 provided inside the drug syringe mounting component 6. The operating rod 21 is pushed to the rear end side by the syringe cover 8, and this actuates the syringe cover detection switch 22, which causes the controller 23 (discussed below) to detect the mounting of the syringe cover 8.

The controller 23 is disposed around the outer periphery of the drug syringe mounting component 6, and controls the operation of the various electrical parts of the drug injection device 100.

Further, the acceleration sensor 24 is connected to the controller 23. That is, the acceleration sensor 24 is disposed at a place that is away from the center of gravity of the main body case 1. Consequently, the acceleration sensor 24 can more properly detect acceleration with respect to this main body case 1.

Here, the acceleration sensor 24 is a three-dimensional acceleration sensor, for example. A three-dimensional acceleration sensor is suited to the detection of vibration or the detection of falling, as discussed below. If only the inclination of the device main body is to be detected, for example, then either a three-dimensional acceleration sensor or a two-dimensional acceleration sensor may be used.

1.2 Electrical Configuration of Drug Injection Device 100

Figure 4:
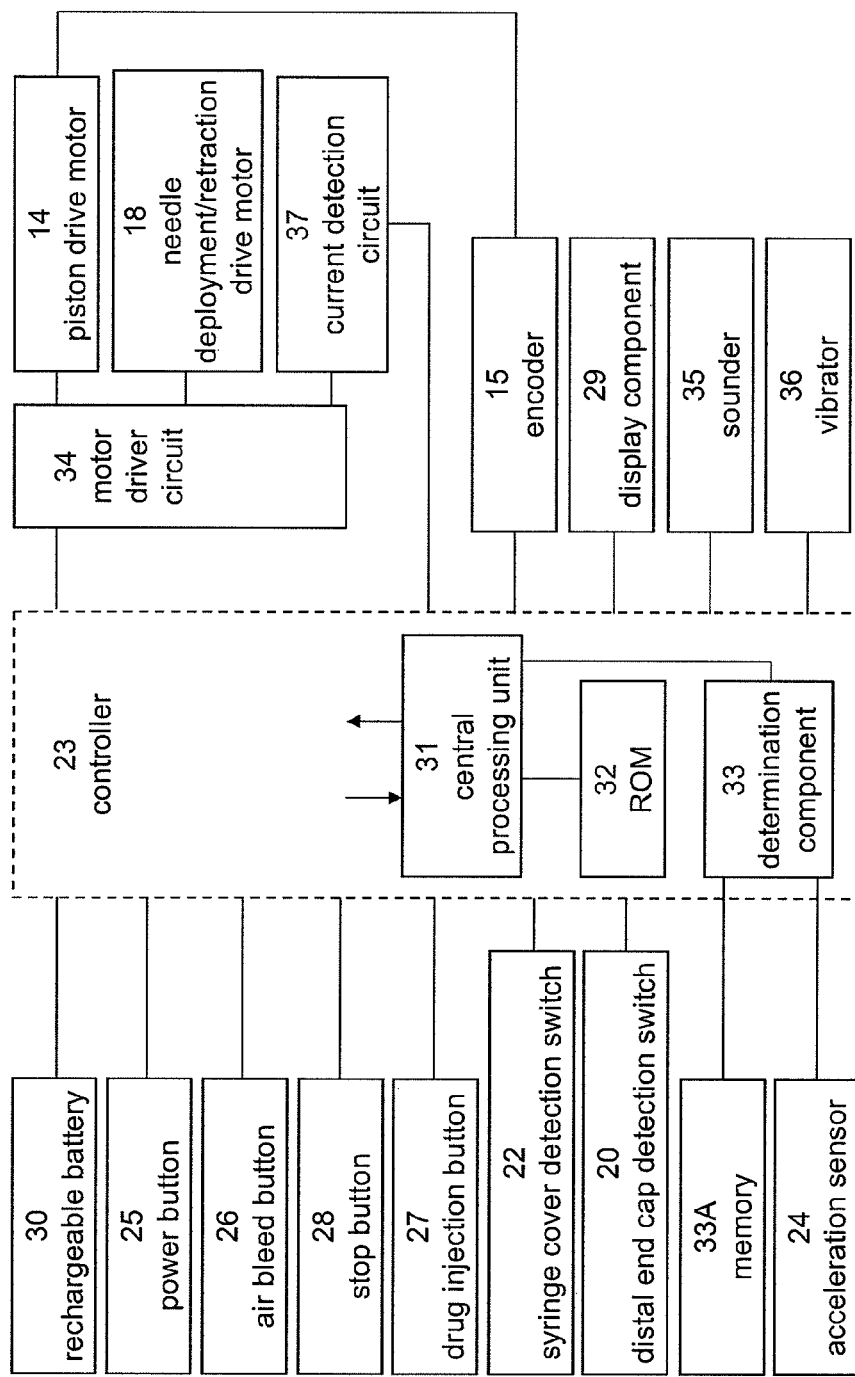
FIG. 4 is a control block diagram schematically illustrating the electrical configuration of this drug injection device.

FIG. 4 is a control block diagram schematically illustrating the electrical configuration of the drug injection device 100. The controller 23 is a control circuit made up of a microprocessor or the like, for example. The rechargeable battery 30 shown in FIG. 4 is connected to the controller 23 and other electrically driven parts. The state of electrical connection between this rechargeable battery 30 and the other electrically driven parts is omitted from the drawings for the sake of simplicity.

The controller 23 includes a central processing unit 31, a ROM 32, and a determination component 33. The central processing unit 31 controls the operation of the various blocks shown in FIG. 4. The program that executes this operational control is written to the ROM 32. The determination component 33 connected to the central processing unit 31 is also connected to a memory 33A and the acceleration sensor 24.

The memory 33A, as discussed below, stores first and second set values detected by the acceleration sensor 24. The determination component 33 is designed to compare the acceleration detected by the acceleration sensor 24 with the first and second set values, and control various operations.

A motor driver circuit 34 is connected to the piston drive motor 14 and the needle deployment/retraction drive motor 18, and a current detection circuit 35 is connected to this motor driver circuit 34. Further, a sounder 35 and a vibrator 36 for issuing warnings are connected to the controller 23.

1.3 Operational Control of Drug Injection Device 100

The various operational controls of the drug injection device 100 having the above electrical configuration will now be described through reference to a flowchart.

1.3.1 Control of Air Bleed Operation

Figure 5:
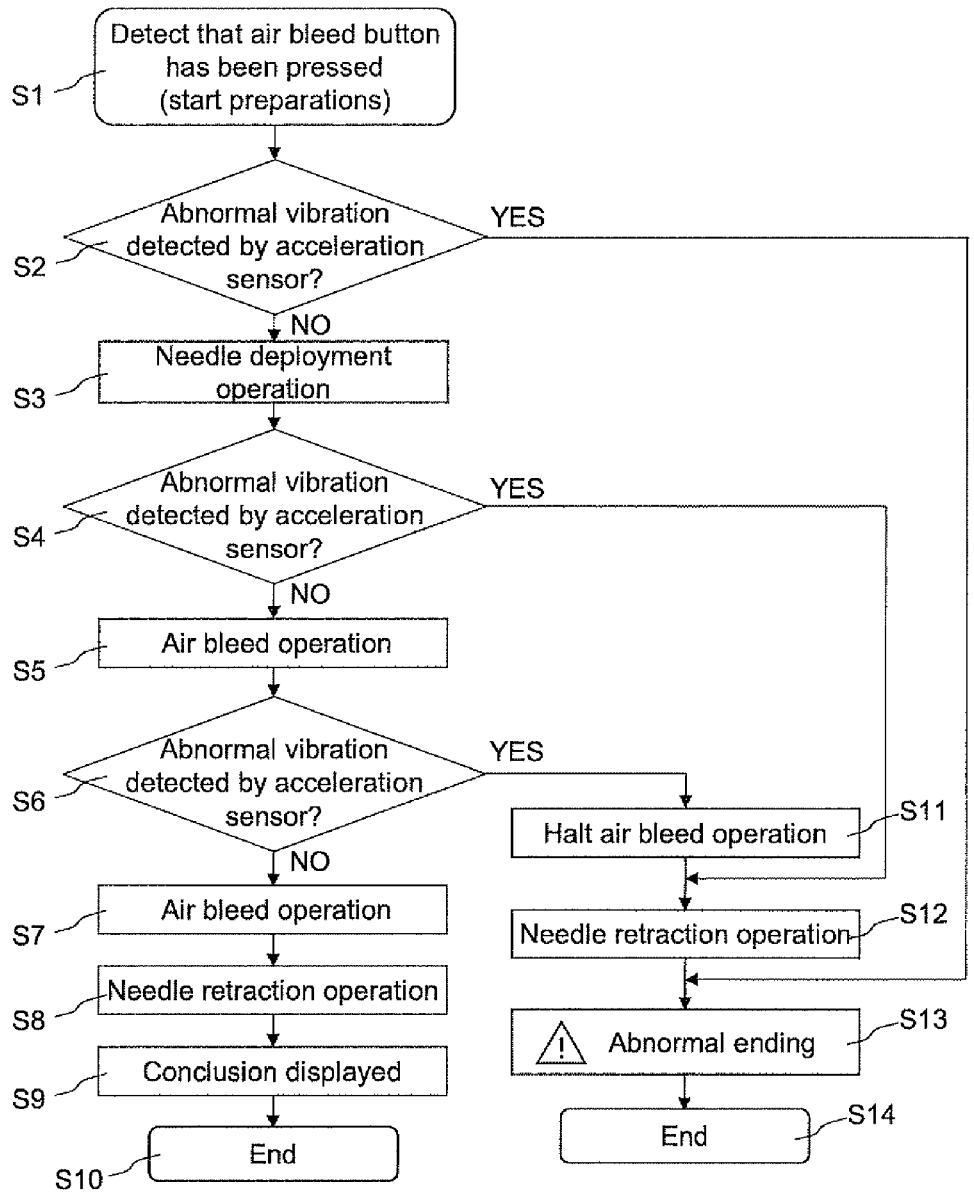
FIG. 5 is a flowchart of the operation control in this drug injection device.

FIG. 5 is a flowchart of the control during the air bleed operation of the drug injection device 100. We will assume a state in which the drug syringe 7 has already been mounted in the drug syringe mounting component 6 as shown in FIG. 2.

Step S1: When the air bleed button 26 (FIGS. 1 and 4) is pressed by the user, this is detected by the controller 23.

Step S2: The determination component 33 of the controller 23 uses the acceleration sensor 24 to perform abnormal vibration detection. An abnormal vibration here is a state in which hand shake is occurring, for example. When abnormal vibration is detected, the flow proceeds to step S13, this abnormality is displayed (such as a display of "abnormal ending") on the display component 29 (FIGS. 1 and 4), and the operation is ended at step S14.

Abnormal vibration detection is performed as follows. The controller 23 determines whether or not the value indicating acceleration detected by the acceleration sensor 24 exceeds a first set value (specific value) stored in the memory 33A (or is at least the first set value), and, if the value exceeds, determines that there is abnormal vibration.

Step S3: Needle deployment is begun if no abnormal vibration was detected in step S2. "Needle deployment" here is an operation in which the injection needle 9 is pushed out from the injection needle let-in/let-out opening 5, as shown in FIG. 3. More specifically, the needle deployment/retraction drive motor 18 is driven at a command from the controller 23, the drug syringe mounting component 6 is moved to the injection needle let-in/let-out opening 5 side, and the injection needle 9 is pushed out through the injection needle let-in/let-out opening 5.

Step S4: During this needle deployment operation, the determination component 33 uses the acceleration sensor 24 to perform abnormal vibration detection. If abnormal vibration is detected, the flow proceeds to step S12, and needle retraction is executed. "Needle retraction" here is an operation in which the injection needle 9 is pulled back through the injection needle let-in/let-out opening 5 to inside the distal end cap 3. More specifically, the needle deployment/retraction drive motor 18 is rotated in the opposite direction from that during needle deployment at a command from the controller 23, and the injection needle 9 is pulled along with the drug syringe mounting component 6 back through the injection needle let-in/let-out opening 5 to inside the distal end cap 3 as shown in FIG. 2. Here again, the operation is halted in step S14 via step S13.

Step S5: On the other hand, if no abnormal vibration is detected in step S4, an air bleed operation is begun. The "Air bleed operation" here means an operation for purging air from the drug syringe 7 and the injection needle 9. More specifically, the piston drive motor 14 is driven at a command from the controller 23 from a state in which the injection needle 9 is protruding from the injection needle let-in/let-out opening 5 as shown in FIG. 3, and the rubber seal 11 is pushed in by the piston 12 by a specific amount to the injection needle let-in/let-out opening 5 side. Consequently, a specific amount of the drug 10 is ejected from the injection needle 9, and air is purged from the drug syringe 7 and the injection needle 9.

The amount of movement of the piston 12 here is controlled by controlling the amount of rotation of the piston drive motor 14 using the encoder 15.

Step S6: During this air bleed operation, the determination component 33 also performs abnormal vibration detection with the acceleration sensor 24. If abnormal vibration is detected, the flow proceeds to step S11, and the air bleed operation is halted. Then, the operation is ended via steps S12, S13, and S14.

Step S7: If no abnormal vibration is detected in step S6, the air bleed operation is concluded.

Step S8: Upon conclusion of the air bleed operation, just as in step S12, needle retraction is executed at a command from the controller 23, and the drug injection device 100 goes from the state shown in FIG. 3 to that in FIG. 2.

Step S9: The fact that the air bleed operation has been concluded is displayed on the display component 29.

Step S10: The operation is ended.

Step S11: As mentioned above, if abnormal vibration is detected in step S6, the air bleed operation is halted.

Step S12: As discussed above, needle retraction is executed if abnormal vibration is detected in step S4, or after the air bleed operation has been halted in step S11.

Step S13: As discussed above, the display component 29 (FIG. 1) displays an abnormality (such as a display of "abnormal ending") if abnormal vibration is detected in step S2, or after the needle retraction operation in step S12.

Step S14: The operation is ended.

1.3.2: Control of Drug Injection Operation

Figure 6:
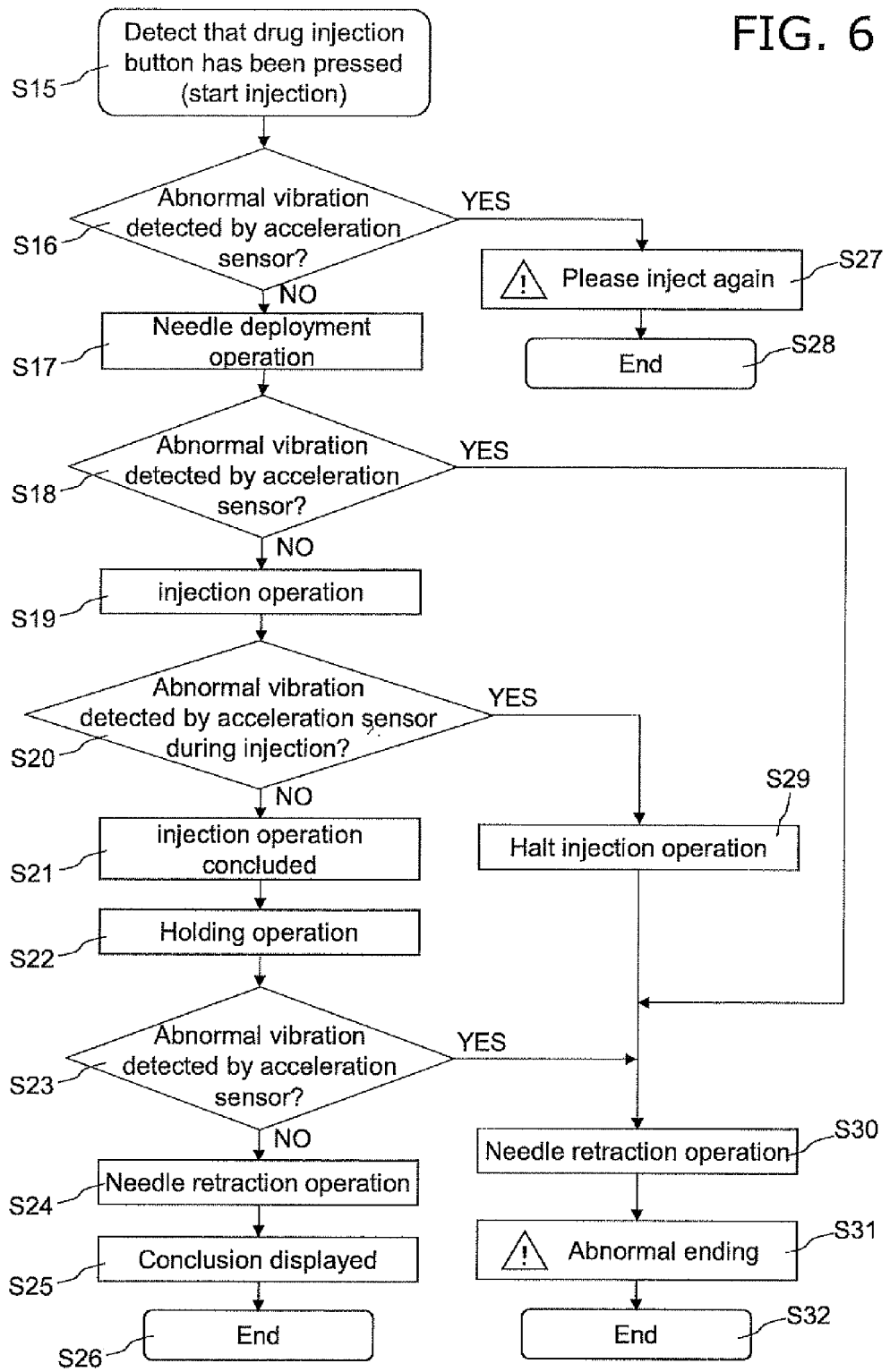
FIG. 6 is a flowchart of the operation control in this drug injection device.

FIG. 6 is a flowchart of the control during the operation in which the drug injection device 100 injects the drug 10 into a patient.

Step S15: The drug injection button 27 (FIGS. 1 and 4) is pressed by the user, and this is detected by the controller 23.

Step S16: The determination component 33 of the controller 23 uses the acceleration sensor 24 to perform abnormal vibration detection. "Abnormal vibration," as mentioned above, is a state in which hand shake is occurring, for example. When abnormal vibration is detected, the flow proceeds to step S27, and a display recommending that the operation be performed again (such as "Please inject again") is shown on the display component 29 (FIGS. 1 and 4). The operation is then ended at step S28.

Step S17: If abnormal vibration is not detected in step S16, the needle deployment operation is begun. "Needle deployment" here is an operation in which the injection needle 9 is pushed out from the injection needle let-in/let-out opening 5 as shown in FIG. 3, and as discussed above, the drug syringe mounting component 6 is moved to the injection needle let-in/let-out opening 5 side by the needle deployment/retraction drive motor 18 at a command from the controller 23.

At this point, the injection needle let-in/let-out opening 5 of the distal end cap 3 is already being pressed against the site on the body to receive the injection. Thus, in step S17, the injection needle 9 is moved toward the body, and the injection needle 9 is plunged into the body.

Step S18: During this needle deployment operation, the determination component 33 uses the acceleration sensor 24 to perform abnormal vibration detection. If abnormal vibration is detected, the flow proceeds to step S30, and needle retraction is executed. As discussed above, "needle retraction" here is an operation in which the injection needle 9 is pulled back through the injection needle let-in/let-out opening 5 to inside the distal end cap 3 as shown in FIG. 2. More specifically, the needle deployment/retraction drive motor 18 is rotated in the opposite direction from that during needle deployment at a command from the controller 23, and the injection needle 9 is pulled along with the drug syringe mounting component 6 back through the injection needle let-in/let-out opening 5 to inside the distal end cap 3 as shown in FIG. 2.

Step S19: If no abnormal vibration is detected in step S18, the controller 23 begins the injection of the drug 10. The injection of the drug 10 here is an operation in which, as shown in FIG. 3, the piston drive motor 14 is driven at a command from the controller 23 in a state in which the injection needle 9 is sticking out from the injection needle let-in/let-out opening 5, and the rubber seal 11 is pushed in by the piston 12 by a specific amount to the injection needle let-in/let-out opening 5 side. As a result, a specific amount of the drug 10 is injected from the injection needle 9 into the body.

The amount of movement of the piston 12 here is controlled by controlling the amount of rotation of the piston drive motor 14 using the encoder 15. This movement amount is recorded to the memory 33A in FIG. 4 by a physician, and this sets the amount of drug 10 to be injected each time for each user (injection amount).

Step S20: During this drug injection operation, the determination component 33 uses the acceleration sensor 24 to perform abnormal vibration detection. If abnormal vibration is detected, the flow proceeds to step S29 and the injection operation is halted. At the point when the injection operation is halted in step S29, the injection needle 9 is in a state of having been inserted into the body. Therefore, the needle retraction operation of the next step S30 is not begun right away, and instead the movement of the piston 12 and the drug syringe mounting component 6 is stopped for six seconds (holding operation), for example, and when it is judged that the drug 10 has penetrated into the body, the needle retraction operation is begun, and the injection needle 9 is pulled out of the body. After this, the operation is ended via steps S31 and S32.

Step S21: If no abnormal vibration is detected in step S20, the injection operation is concluded.

Step S22: Just as in step S29, movement of the piston 12 and the drug syringe mounting component 6 is stopped for six seconds (holding operation), for example. This allows the drug 10 to penetrate into the body without fail.

Step S23: During this holding operation, abnormal vibration detection is performed with the acceleration sensor 24, and if abnormal vibration is detected, the operation is ended via steps S30, S31, and S32.

Step S24: If no abnormal vibration is detected in step S23, the controller 23 retracts the injection needle 9 into the distal end cap 3 so that the state changes from that in FIG. 3 to that in FIG. 2, and this pulls the injection needle 9 out of the body.

Step S25: The controller 23 displays on the display component 29 the fact that the injection of the drug 10 has been concluded.

Step S26: The operation is ended.

Step S27: As discussed above, if no abnormal vibration is detected in step S16, a display recommending that the operation be performed again (such as "Please inject again") is shown on the display component 29 (FIGS. 1 and 4).

Step S28: The operation is ended.

Step S29: As discussed above, if no abnormal vibration is detected in step S20, the injection operation is halted.

Step S30: As discussed above, if abnormal vibration is detected in step S18 or step S23, or if the injection operation is halted in step S29, then the needle retraction operation is executed.

Step S31: A display indicating an abnormality (such as a display of "abnormal ending") is shown on the display component 29 (FIG. 1).

Step S32: The operation is ended.

1.3.3: Control of Periodic Monitoring

Figure 7:
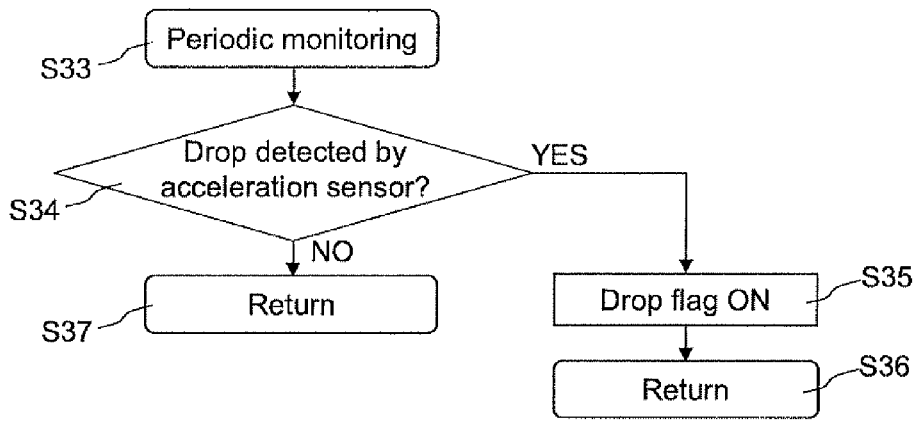
FIG. 7 is a flowchart of the operation control in this drug injection device.

FIG. 7 shows the operation in periodic monitoring by the drug injection device 100.

Step S33: Periodic monitoring is performed by the determination component 33 of the controller 23. The periodic monitoring is performed both in an OFF state in which the power button 25 has not been pressed, and in an ON state in which the power button 25 has been pressed.

Step S34: The determination component 33 uses the acceleration sensor 24 to perform drop detection. "Drop detection" here is to detect with the acceleration sensor 24 that a large acceleration has been applied.

In addition to the above-mentioned first set value used for acceleration, a second set value is also stored in the memory 33A shown in FIG. 4. In drop detection, it is determined that the device has been dropped if an acceleration that is over a second set value (or at least a second set value) is detected.

That is, in abnormal vibration detection by means of hand shake or the like as discussed above, the determination component 33 determines whether or not the acceleration sensor 24 has detected an acceleration that is over the first set value in the memory 33A, and determines that there is abnormal vibration if this value has been exceeded. On the other hand, in drop detection, the determination component 33 determines whether or not acceleration has been detected that exceeds a second set value that is greater than the first set value, and determines that the device has been dropped if this value is exceeded.

Step S35: If a drop is detected in step S34, drop information is stored in the memory 33A at a command from the controller 23, and a drop flag is switched on.

Step S36: The flow goes back to step S33, and periodic monitoring is continued.

Step S37: If no drop was detected in step S34, the flow goes back to step S33, and periodic monitoring is continued.

1.3.4: Control After Drop Detection

Figure 8:
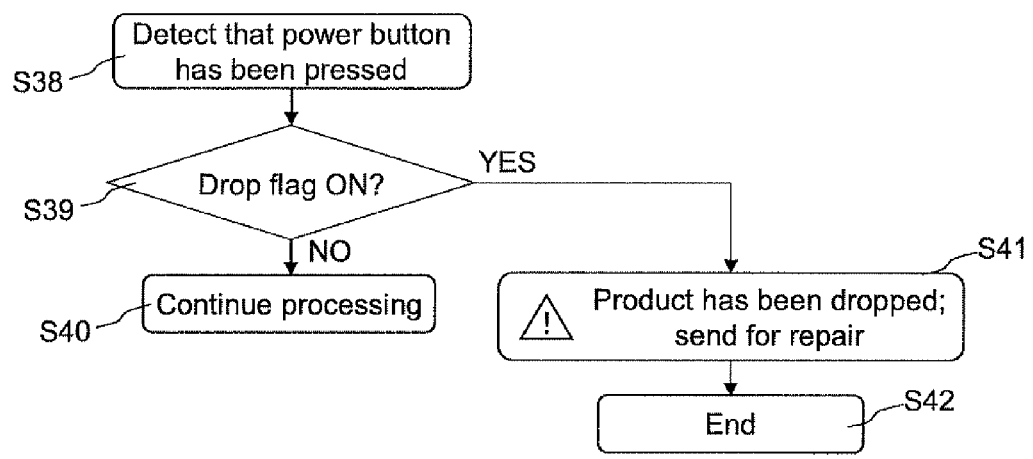
FIG. 8 is a flowchart of the operation control in this drug injection device.

FIG. 8 shows the operation of the drug injection device 100 when the power is on.

Step S38: The controller 23 detects that the power button 25 (FIGS. 1 and 4) has been pressed.

Step S39: The determination component 33 of the controller 23 determines whether the drop flag in the memory 33A (FIG. 4) is on or off (whether or not a flag is active). If the drop flag is off, that is, if there is no drop, the flow proceeds to step S40. If the drop flag is on, that is, if there is a drop, the flow proceeds to step S41.

Step S40: If it is determined in step S39 that there was no drop, the flow proceeds to the next processing. The "next processing" is the processing shown in FIGS. 5 and 6, for example.

Step S41: On the other hand, if it is determined in step S39 that there was a drop, then a display indicating that the device has been dropped, and a display recommending that the device be serviced (such as a display of "Product has been dropped; send for repair") are made on the display component 29 shown in FIG. 1.

Step S42: The operation is ended.

1.4: Features of Drug Injection Device 100

1.4.1

As discussed above, the drug injection device 100 pertaining to this embodiment comprises the main body case 1 having the injection needle let-in/let-out opening 5, the drug syringe mounting component 6 provided in the main body case 1, the piston 12 provided movably with respect to the drug syringe mounting component 6, the piston drive motor 14 that drives the piston 12, the controller 23 that is electrically connected to the piston drive motor 14, and the acceleration sensor 24 that is electrically connected to the controller 23. This constitution allows the drug to be injected properly.

Specifically, with this embodiment, since the acceleration sensor 24 is connected to the controller 23, any abnormal operation of the main body case 1, such as hand shake, can be detected by the acceleration sensor 24. The injection of the drug can be carried out properly by controlling the operation of the drug injection device 100 on the basis of this detection of abnormal operation.

1.4.2

With the drug injection device 100 pertaining to this embodiment, the acceleration sensor 24 is installed at a position that is away from the center of gravity of the main body case 1, and this affords better detection of acceleration with respect to the main body case 1.

1.4.3

With the drug injection device 100 pertaining to this embodiment, if the controller 23 detects through the acceleration sensor 24 an acceleration that exceeds a first set value (or that is at least the first set value), then movement of the piston 12 to the injection needle let-in/let-out opening side is stopped, and this makes the drug injection device 100 safer to use.

1.4.4

With the drug injection device 100 pertaining to this embodiment, the drive mechanism 18 is provided for driving the drug syringe mounting component 6, and if the acceleration sensor 24 detects an acceleration that is at least the first set value, the controller 23 stops the drug syringe mounting component 6 from moving to the injection needle let-in/let-out opening side, or retracts the drug syringe mounting component 6 in a direction away from the injection needle let-in/let-out opening 5. This makes the drug injection device 100 safer to use.

Also, at this point, after the movement of the drug syringe mounting component 6 to the injection needle let-in/let-out opening side has been halted for a specific length of time, the drug syringe mounting component 6 is retracted away from the injection needle let-in/let-out opening 5, and this makes the drug injection device 100 even safer to use.

1.4.5

With the drug injection device 100 pertaining to this embodiment, drop information is stored and operation is performed according to whether or not there is drop information, and this makes the drug injection device 100 even safer to use.

2. Other Embodiments

An embodiment of the present invention was given above, but the present invention is not limited to what was given in the above embodiment, and a person skilled in the art will foresee modifications and applications on the basis of the text of this Specification and known technology, all of which is encompassed by the scope for which protection is sought.

3. Modification Example of Air Bleed Control

A modification of the method for controlling the air bleed operation will now be given.

Figure 9:
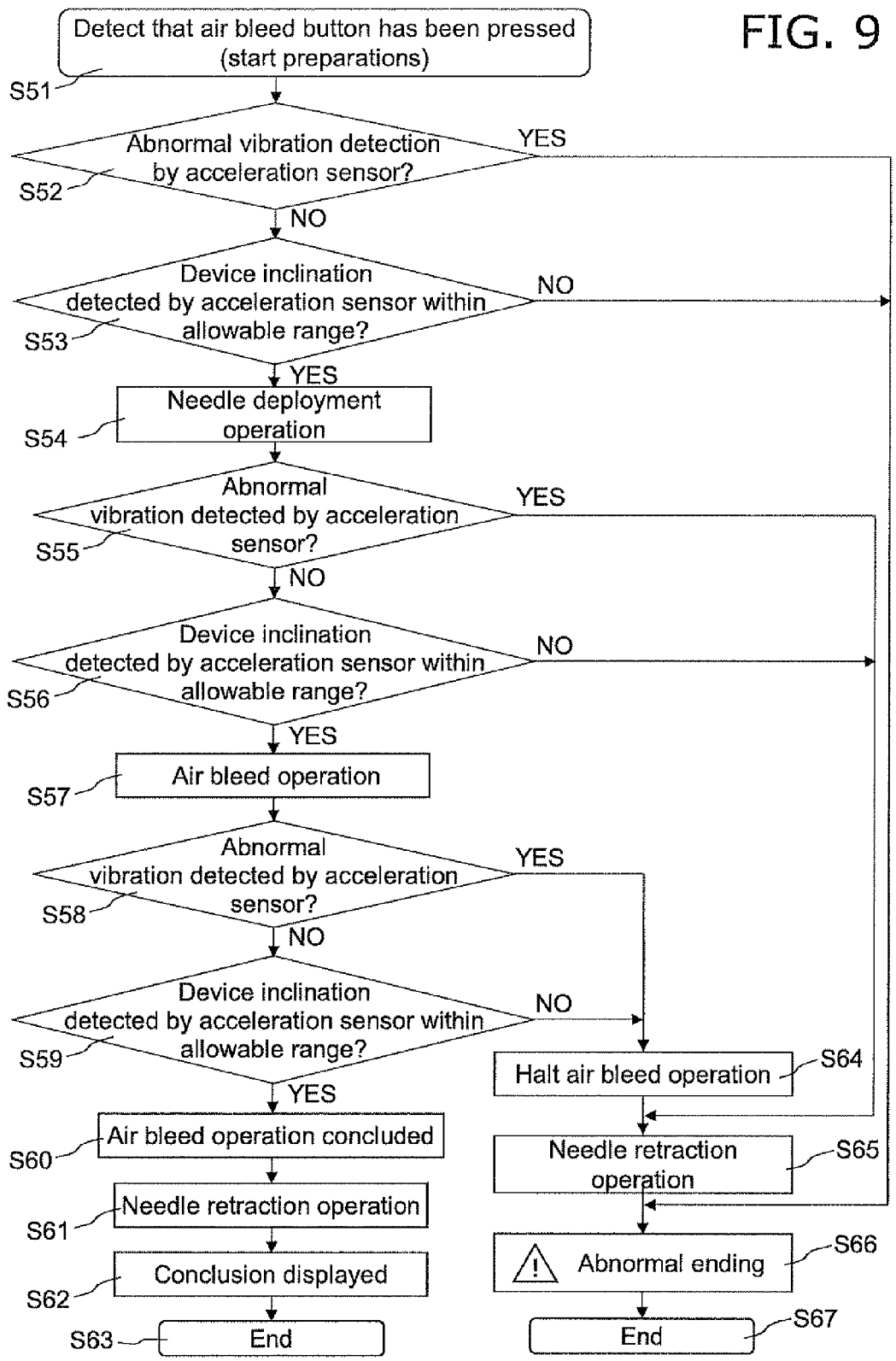
FIG. 9 is a flowchart of the operation control in a modification example of this drug injection device.

FIG. 9 is a modification of the method for controlling the air bleed operation of the drug injection device 100, and is a flowchart of the control operation when the acceleration sensor has a device inclination detection function in addition to the above-mentioned abnormal vibration detection function. Here, the acceleration sensor can be a three-dimensional acceleration sensor just as in the above embodiment, but if only the inclination of the device main body is to be detected, for example, then either a three-dimensional acceleration sensor or a two-dimensional acceleration sensor may be used.

During the control operation in FIG. 9, as shown in FIG. 2, let us assume that the drug syringe 7 has already been mounted in the drug syringe mounting component 6.

Step S51: When the user presses the air bleed button 26 (FIGS. 1 and 4), this is detected by the controller 23 (see FIG. 4), and an air bleed operation is begun.

Step S52: The determination component 33 of the controller 23 uses the acceleration sensor 24 (see FIGS. 2 and 4) to perform abnormal vibration detection. The "abnormal vibration" here is a state in which hand shake is occurring, for example. If abnormal vibration has been detected, the flow proceeds to step S66, and a display indicating an abnormality (such as a display of "abnormal ending") is shown on the display component 29 (FIGS. 1 and 4). The operation is then ended in step S67.

The abnormal vibration detection here is carried out as follows. The determination component 33 determines whether or not the value indicating acceleration detected by the acceleration sensor 24 exceeds a first set value (specific value) stored in the memory 33A (or is at least the first set value), and if this value is exceeded, it is determined that there is abnormal vibration.

Step S53: The determination component 33 of the controller 23 further performs device inclination detection with the acceleration sensor 24. Here, "inclination detection" refers to confirming that the device is vertically oriented by determining the inclination of the device main body with respect to a vertical line, in which the up direction is the direction of injecting into the user's skin, in order to execute the air bleed operation without fail, for example.

If this device inclination detection concludes that there is an abnormality, the flow proceeds to step S66, and a display indicating an abnormality (such as a display of "abnormal ending") is shown on the display component 29 (FIGS. 1 and 4). The operation is then ended in step S67.

The inclination detection for the device main body is carried out as follows. The determination component 33 determines whether or not a value indicating the inclination angle detected by the acceleration sensor 24 exceeds a third set value (specific value) stored in the memory 33A (or is at least the third set value), and if this value is exceeded, it is determined that the inclination of the device main body is abnormal.

The third set value can be preset in a memory or the like, and is a set value with a range of ±45 degrees with respect to the vertical direction, for example. A set value with a range of ±30 degrees is even better.

Inclination of the main body can be detected more accurately by performing the inclination detection after the abnormal vibration detection.

Step S54: If no abnormal vibration is detected in step S52, and no abnormal inclination of the device main body is detected in step S53, needle deployment is begun. Here, "needle deployment" is an operation in which the injection needle 9 is pushed out from the injection needle let-in/let-out opening 5 as shown in FIG. 3. More specifically, the needle deployment/retraction drive motor 18 is driven at a command from the controller 23, the drug syringe mounting component 6 is moved to the injection needle let-in/let-out opening 5 side, and the injection needle 9 is pushed out from the injection needle let-in/let-out opening 5.

Step S55: During this needle deployment operation, the determination component 33 uses the acceleration sensor 24 to perform abnormal vibration detection. If abnormal vibration is detected, the flow proceeds to step S65, and need retraction is executed. "Needle retraction" here is an operation in which the injection needle 9 is pulled back through the injection needle let-in/let-out opening 5 to inside the distal end cap 3, as shown in FIG. 2. More specifically, the needle deployment/retraction drive motor 18 is rotated in the opposite direction from that during needle deployment at a command from the controller 23, and the injection needle 9 is pulled along with the drug syringe mounting component 6 back through the injection needle let-in/let-out opening 5 to inside the distal end cap 3 as shown in FIG. 2. Here again, the operation is halted in step S67 via step S66.

Step S56: Furthermore, during the needle deployment operation, the determination component 33 performs abnormal inclination detection for the device main body with the acceleration sensor 24. If abnormal inclination is detected, the flow proceeds to step S65, and needle retraction is performed. Here again, the operation is halted in step S67 via step S66.

Step S57: On the other hand, if no abnormal vibration is detected in step S55, and no abnormal inclination of the device main body is detected in step S56, an air bleed operation is begun. The "Air bleed operation" here is an operation in which air is purged from the drug syringe 7 and the injection needle 9. More specifically, as shown in FIG. 3, from a state in which the injection needle 9 is protruding from the injection needle let-in/let-out opening 5, the piston drive motor 14 is driven at a command from the controller 23, and the rubber seal 11 is pushed in by the piston 12 by a specific amount to the injection needle let-in/let-out opening 5 side. Consequently, a specific amount of the drug 10 is ejected from the injection needle 9, and the air is purged from the drug syringe 7 and the injection needle 9.

The amount of movement of the piston 12 here is controlled by controlling the amount of rotation of the piston drive motor 14 using the encoder 15.

Step S58: Also during this air bleed operation, the determination component 33 performs abnormal vibration detection with the acceleration sensor 24. If abnormal vibration is detected, the flow proceeds to step S64, and the air bleed operation is halted. The operation is then ended via steps S65, S66, and S67.

Step S59: Also during this air bleed operation, the determination component 33 performs abnormal inclination detection for the device main body with the acceleration sensor 24. If abnormal inclination is detected, the flow proceeds to step S64, and the air bleed operation is halted. The operation is then ended via steps S65, S66, and S67.

Step S60: If no abnormal vibration is detected in step S58, and no abnormal inclination of the device main body is detected in step S59, the air bleed operation is concluded.

Step S61: Upon conclusion of the air bleed operation, needle retraction is performed at a command from the controller 23 just as in step S65, and the drug injection device 100 changes from the state shown in FIG. 3 to that in FIG. 2.

Step S62: The fact that the air bleed operation has been concluded is displayed on the display component 29.

Step S63: The operation is ended.

Step S64: As mentioned above, if abnormal vibration is detected in step S58, or if abnormal inclination of the device main body is detected in step S59, the air bleed operation is halted.

Step S65: As discussed above, needle retraction is executed if abnormal vibration is detected in step S55, or if abnormal inclination of the device main body is detected in step S56, or after the air bleed operation has been halted in step S64.

Step S66: As discussed above, the display component 29 (FIG. 1) displays an abnormality (such as a display of "abnormal ending") if abnormal vibration is detected in step S52, or if abnormal inclination of the device main body is detected in step S53, or after needle retraction in step S65.

Step S67: The operation is ended.

With the above modification example of the drug injection device 100, in addition to the detection of abnormal vibration in the drug injection device 100 by an acceleration sensor, inclination of the device main body is also detected during the air bleed operation, and controlling the operation of the drug injection device 100 is in this way allows the air bleed operation to be carried out more accurately.

The present invention is useful as a drug injection device such as a syringe.

The invention claimed is:

1. A drug injection device, comprising:
   a main body case having an injection needle let-in/let-out opening;
   a syringe unit inside the main body case and configured to be equipped with a drug syringe therein, the syringe unit comprising a piston and a first drive motor which drives the piston;
   a second drive motor configured to drive the syringe unit;
   a controller electrically connected to the first drive motor and the second drive motor; and
   an acceleration sensor electrically connected to the controller and being configured to detect acceleration applied to the main body case,
   wherein the controller stops the syringe unit from moving toward the injection needle let-in/let-out opening, or retracts the syringe unit away from the injection needle let-in/let-out opening, when the acceleration sensor has detected an acceleration of at least a first set value.

2. The drug injection device according to claim 1, wherein the controller stops the syringe unit from moving toward the injection needle let-in/let-out opening for a specific length of time, and then retracts the syringe unit away from the injection needle let-in/let-out opening, when the acceleration sensor has detected an acceleration of at least a first set value.

3. The drug injection device according to claim 1, wherein the acceleration sensor is configured to detect vibration of the drug injection device.

4. The drug injection device according to claim 3, wherein the controller is configured to determine whether the vibration detected by the acceleration sensor exceeds a first set value.

5. The drug injection device according to claim 1, wherein the acceleration sensor is disposed at a position that is spaced from a center of gravity of the main body case.

6. The drug injection device according to claim 1, wherein the controller stops the piston from moving toward the injection needle let-in/let-out opening when the acceleration sensor has detected an acceleration of at least a first set value.

7. The drug injection device according to claim 6, wherein the controller stores abnormality information in a memory when the acceleration sensor has detected an acceleration of at least a second set value that is greater than the first set value.

8. The drug injection device according to claim 7, wherein the abnormality information is information indicating that the main body case has been dropped.

9. The drug injection device according to claim 1, wherein the acceleration sensor is configured to further detect information about inclination of the main body case, and
the controller is configured to acquire the information about the inclination of the main body case detected by the acceleration sensor, and based on the acquired information, determines whether or not air bleeding is possible and controls the first drive motor.

10. The drug injection device according to claim 1, wherein the controller stores abnormality information in a memory when the acceleration sensor has detected an acceleration of at least a second set value that is greater than the first set value.

* * * * *